(12) United States Patent
Mische (10) Patent No.: US 7,390,296 B2
(45) Date of Patent: Jun. 24, 2008

(54) INFLATABLE PENILE PROSTHESIS WITH VOLUME DISPLACEMENT MATERIALS AND DEVICES

(75) Inventor: Hans A. Mische, St. Cloud, MN (US)

(73) Assignee: AMS Research Corporation, Minnetonka, MN (US)

( * ) Notice: Subject to any disclaimer, the term of this patent is extended or adjusted under 35 U.S.C. 154(b) by 782 days.

(21) Appl. No.: 10/861,901

(22) Filed: Jun. 4, 2004

(65) Prior Publication Data

US 2005/0014993 A1 Jan. 20, 2005

Related U.S. Application Data

(60) Provisional application No. 60/476,844, filed on Jun. 6, 2003, provisional application No. 60/507,975, filed on Oct. 2, 2003.

(51) Int. Cl.
*A61F 5/00* (2006.01)
(52) U.S. Cl. ........................................................ 600/40
(58) Field of Classification Search ............. 600/38–41; 623/11.11
See application file for complete search history.

(56) References Cited

U.S. PATENT DOCUMENTS

| | | | |
|---|---|---|---|
| 4,201,202 A * | 5/1980 | Finney et al. ................. 600/40 |
| 4,267,829 A | 5/1981 | Burton et al. | |
| 4,383,525 A | 5/1983 | Scott et al. | |
| 4,407,278 A | 10/1983 | Burton et al. | |
| 4,590,927 A | 5/1986 | Porter et al. | |
| 4,651,721 A | 3/1987 | Mikulich et al. | |
| 4,671,261 A | 6/1987 | Fischell | |
| 4,718,410 A | 1/1988 | Hakky | |
| 4,782,826 A | 11/1988 | Fogarty | |
| 4,895,139 A | 1/1990 | Hauschild et al. | |
| 5,010,882 A | 4/1991 | Polyak et al. | |
| 5,048,510 A | 9/1991 | Hauschild et al. | |
| 5,112,295 A | 5/1992 | Zinner et al. | |
| 5,250,020 A * | 10/1993 | Bley ............................ 600/40 |
| 5,263,981 A | 11/1993 | Polyak et al. | |
| 5,704,895 A | 1/1998 | Scott et al. | |

* cited by examiner

*Primary Examiner*—John P Lacyk
(74) *Attorney, Agent, or Firm*—Jose W. Jimenez; Kimberly K. Baxter; Gregory L. Koeller (57) ABSTRACT

A penile prosthesis is provided, which includes a generally cylindrical body portion comprising a cavity with an inner wall, a proximal end, a distal end, and at least one volume-displacing member occupying at least a portion of the cavity, wherein the at least one volume-displacing member is smaller in at least one dimension than the dimensions of the cavity to provide an internal chamber at least partially surrounding the at least one volume-displacing member and adjacent to the inner wall of the cavity. The prosthesis further includes a fluid transfer tube extending from the body portion for transferring fluid to and from the internal chamber, wherein the device is convertible from a flaccid condition to a rigid condition when a sufficient volume of fluid is transferred into the internal chamber to substantially fill the internal chamber.

21 Claims, 6 Drawing Sheets

Fig. 19

US 7,390,296 B2

INFLATABLE PENILE PROSTHESIS WITH VOLUME DISPLACEMENT MATERIALS AND DEVICES

REFERENCE TO RELATED APPLICATIONS

This application claims the benefit of U.S. Provisional applications having Ser. No. 60/476,844, filed Jun. 6, 2003, entitled "IMPROVEMENTS FOR TREATING ERECTILE DYSFUNCTION," and Ser. No. 60/507,975, filed Oct. 2, 2003, entitled "INFLATABLE PENILE PROSTHESIS WITH VOLUME DISPLACEMENT MATERIALS AND DEVICES," which applications are incorporated herein by reference in their entirety.

TECHNICAL FIELD

The present invention relates to systems for treating erectile dysfunction and other urological disorders. In particular, the invention relates to implantable penile prostheses.

BACKGROUND OF THE INVENTION

One common treatment for erectile dysfunction includes the use of a penile implant device. One type of penile implant device includes a pair of cylindrical prostheses that are implanted into the corpus cavernosae of the penis. In some instances, the prostheses are inflatable and are connected to a fluid-filled reservoir through a pump and valve assembly. Such a pump assembly is typically implanted into the scrotum of the patient, and the reservoir is implanted in the abdomen. To activate the penile implant device, the patient actuates the pump using one of a variety of methods that cause fluid to be transferred from the reservoir through the pump and into the prostheses. This results in the inflation of the prostheses and produces rigidity for a normal erection. Then, when the patient desires to deflate the prostheses, a valve assembly within the pump is actuated in a manner such that the fluid in the prostheses is released back into the reservoir. This deflation returns the penis to a flaccid state.

In many of these penile implant devices, the prostheses will be in a relatively collapsed state or condition when deflated and will not again regain significant rigidity until the penile implant device is reactivated, thereby causing at least partial reinflation of the cylinders. In many cases, when the prostheses are in their collapsed state (i.e., the flaccid state of the penis), they may not provide enough support to give the patient a natural feeling of fullness. In addition, these devices require the transfer of a sufficient volume of fluid to change the prostheses from their deflated state to their inflated state, where the amount of fluid to be transferred may directly correlate to the amount of manipulation or steps required to move such a volume of fluid. That is, a greater volume of fluid transfer may require a greater amount of manipulation to transfer such fluid volume to the prostheses. Thus, it is desirable to provide an inflatable prosthetic penile device or system that provides a more natural and full feel of the penis in its flaccid state while requiring a smaller volume of fluid transfer to inflate the prostheses.

SUMMARY OF THE INVENTION

The present invention provides certain advantages relating to the reduced volume of fluid that must be transferred within a system to inflate and deflate implantable penile prostheses. With the devices and methods of the present invention, it may be possible for the system to include a relatively small reservoir for holding the smaller amount of fluid required for the inflation and deflation processes. This is accomplished using a variety of different elongated structures, each of which can be positioned within a cylindrical prosthesis to occupy a portion of the interior cavity of the structure. In other words, when the interior cavities of the devices have at least a portion of their volumes filled with material, the amount of fluid to change the condition of the device is reduced. The use of such volume-occupying devices may provide the further advantages of reducing post-surgical scarring, preventing or eliminating post-surgical shortening or shrinkage of the penis, enhancing patient comfort, and providing a more natural feel to the flaccid penis.

In one aspect of the invention, an implantable penile prosthesis is provided. The prosthesis includes an elongated body portion having an interior cavity connected to a fluid supply, wherein the interior cavity is at least partially filled with a volume-occupying device or member, such as a cylinder or tube. The body portion is inflatable and deflatable through a fluid transfer process, where the fluid supply preferably includes a pumping mechanism. The volume-occupying device may include a liquid-filled bladder, a cylinder containing at least one filament, a malleable member or portion, or a relatively flexible solid mass, such as foam, silicone, or the like, where a wide variety of variations of such devices are possible to achieve a certain amount of rigidity for the prosthesis, both when it is inflated and when it is deflated. It is further contemplated that the volume-occupying device include a plurality of relatively rigid masses that are flexibly connected to each other, such as would be arranged in a "string of beads" or a similar arrangement, where each of the plurality of masses could also be relatively soft or compressible. Further, the volume-occupying device could include a plurality of any of the described members, where these members are not secured to each other.

BRIEF DESCRIPTION OF THE DRAWINGS

The present invention will be further explained with reference to the appended Figures, wherein.

DETAILED DESCRIPTION OF THE PREFERRED EMBODIMENTS

Figure 1:
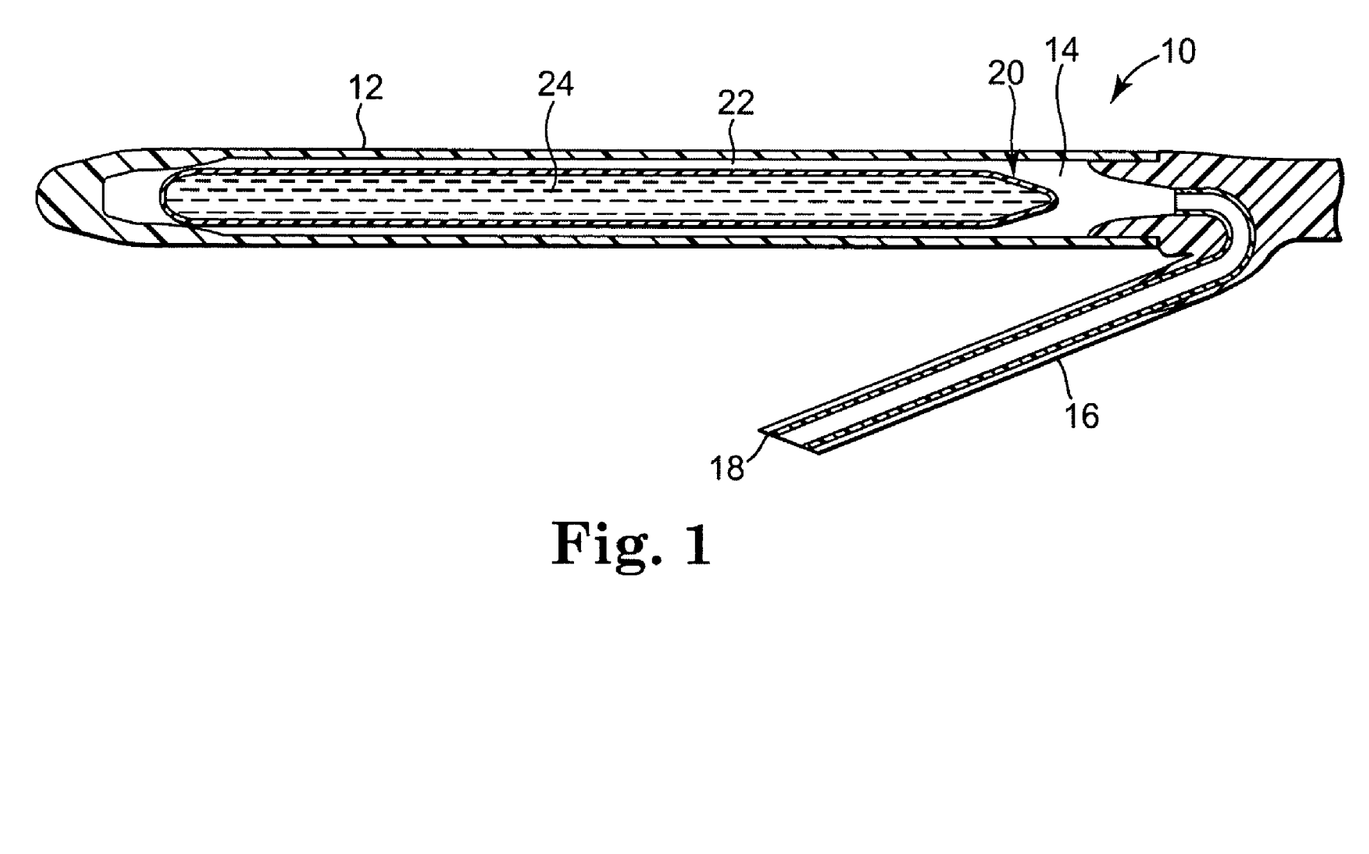
FIG. 1 is a cross-sectional side view of an implantable penile prosthesis device of the present invention, illustrating a sealed bladder within the body portion of the device.

Referring now to the Figures, wherein the components are labeled with like numerals throughout the several Figures, and initially to FIG. 1, one exemplary configuration of an implantable and inflatable penile prosthesis device 10 is illustrated. In most cases, two of these devices 10 will be implanted into the corpus cavernosae of the penis. The device 10 generally includes an inflatable cylindrically shaped body portion 12 having an interior cavity 14 that extends along at least a portion of the length of the body portion 12. The device 10 further includes a tube 16 that extends from the body portion 12 and is used to transport an inflation fluid to and from the interior cavity 14. A distal end 18 of the tube 16 is in fluid communication with a pump assembly and supply reservoir (not shown) that provide a sufficient amount of fluid to inflate the body portion 12, as described in further detail below. The body portion 12 may be formed of a number of different materials that provide the desired strength, flexibility, and expandability to the device 10, such as silicone or the like. Body portion 12 is further preferably selected to have a certain size and shape to best accommodate the anatomical characteristics of the patient.

The various embodiments of a penile prosthesis device described herein are preferably a component of a penile implant device or system, with two such devices being connected to a fluid-filled reservoir and pump assembly that transfers fluid to and from the penile prosthesis devices. Typically, some manipulation or activation of the pump assembly is required by the user to change the state of the penile prosthesis device or devices. That is, the user typically will actuate the pump using one of a wide variety of methods and mechanisms that cause fluid to be transferred between the reservoir and the penile prosthesis devices. The penile prosthesis devices of present invention may be used in the type of system often referred to as a three-piece system, which includes a reservoir, a pump and valve assembly, and a pair of penile prostheses. Alternatively, the penile prosthesis devices of the present invention may be used in the type of system often referred to as a two-piece system, which typically differs from a three-piece system in that it does not include a reservoir that is separate from the pump. Systems of this type are described, for example, in U.S. Pat. Nos. 4,651,721; 4,895,139; 5,010,882; 5,048,510; and 5,263,981, the entire contents of which are incorporated herein by reference. In these types of systems, the pump stores the fluid of the system, thereby also functioning as a reservoir. The pump of this type of system is typically implanted in the scrotum and directly connected to cylinders or penile prosthesis devices. The use of such systems often involves steps such as manipulating a pump body to activate the pump, then repeatedly squeezing and releasing the pump to transfer fluid to the cylinders. The penile prosthesis devices of the present invention are appropriate for use in both two-piece and three-piece systems of the type described above, or may be used with any other penile implant systems that utilize cylindrical implants or prostheses.

As described herein, inflation and deflation of the various devices of the present invention may or may not involve changes in the outer dimensions of the device, such as the body portion 12 of FIG. 1. That is, in some cases, inflation of a device does not cause an actual change the outer dimensions of the device, although the device may become more rigid, such as by the addition of fluid to the device. However, in other cases, a device that is considered to be inflated will be larger in at least one dimension than a device that is considered to be deflated.

Referring again to FIG. 1, the device 10 further includes a bladder 20 positioned within the interior cavity 14 of the body portion 12. The bladder 20 is preferably elongated and generally cylindrical in shape, as shown, and sized to be at least slightly smaller in both length and diameter than the interior cavity 14 so that a space 22 is provided between the bladder 20 and the interior walls of the body portion 12. The bladder 20 contains a volume of fluid 24 that is sealed from the interior cavity 14 so that the fluid 24 within the bladder 20 is not in fluid communication with the fluid provided by the tube 16 to the interior cavity 14 for inflation of the body portion 12. The bladder 20 may be made of a wide variety of materials that are compatible with both the fluid that enters the interior cavity 14 and the space 22, and the fluid 24 within the bladder 20. In this way, fluids that contact the walls of the bladder 20 do not cause any deterioration of the bladder material. The material from which the bladder 20 is made is also preferably sufficiently flexible to generally conform to the shape of the interior cavity 14 when the body portion 12 is in its deflated condition. Thus, the bladder material may be relatively thin, which can further contribute to a more natural feel to the body portion 12. The bladder material is also preferably strong enough to withstand any external pressure without sustaining damage, such as pressure from the fluid provided to the interior cavity 14. Materials that may be used for the bladder 20 include polymeric materials such as silicone polymers, PTFE fluoropolymers (e.g., materials provided under the trade designation "Teflon"), or polyurethanes, for example. As with other materials and fluids described relative to the present invention, the materials used for the bladder 20 should be a biocompatible and medical grade material.

The bladder 20 is preferably pre-filled with a desired fluid or material 24 prior to insertion of the bladder 20 into the cavity 14. Although it is possible that the bladder 20 may be filled after it is placed within the cavity 14, it may be more difficult to properly seal the bladder 20 after it is within the cavity 14. The bladder 20 is preferably completely sealed so that the volume of the bladder 20 remains constant and so that the fluid 24 does not mix with the fluid within the interior chamber 14. The amount of fluid or material 24 placed within the bladder 20 is preferably selected to provide a bladder 20 having sufficient support to give a desired level of rigidity to the bladder 20 and the body portion in which it is positioned, without making the bladder excessively rigid. Further, when the volume of fluid or material 24 provided is less than the volumetric capacity of the bladder 20, the bladder 20 will be at least partially compressible when fluid is transferred under pressure to the cavity 14 for inflation of the body portion 12. The fluid or material itself is preferably an incompressible material, however, to maintain a certain volume within the bladder 20, although it is possible that a compressible material be used within the bladder 20. Exemplary fluids or materials 24 that can be used within the bladder 20 include water, saline, gelatin or other gel materials, glycerin, oil, and the like, or any combination of such exemplary materials.

The size of the bladder 20 relative to the size of the interior cavity 14 is preferably designed or selected so that the bladder 20 is sufficiently large to reduce the volume of fluid that needs to be transferred from the reservoir to the space 22 within the interior cavity 14 to achieve a certain amount of rigidity of the body portion 12 as compared to a device that does not contain such a bladder. However, the size of the bladder 20 should not be so large that it blocks fluid from entering and exiting the cavity 14 through the tube 16 during inflation and deflation of the device. The size of the bladder 20 should further be selected to provide a certain desired level of flaccidity to the body portion 12 when it is in its deflated state.

Figure 2:
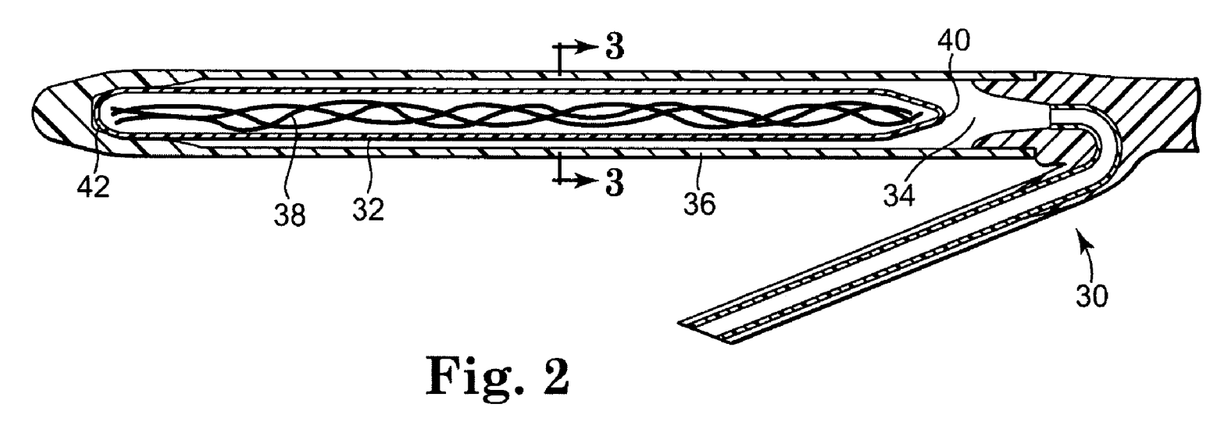
FIG. 2 is a cross-sectional side view of another embodiment of an implantable penile prosthesis device, illustrating a collapsible cylinder within the body portion of the device.
Figure 3:
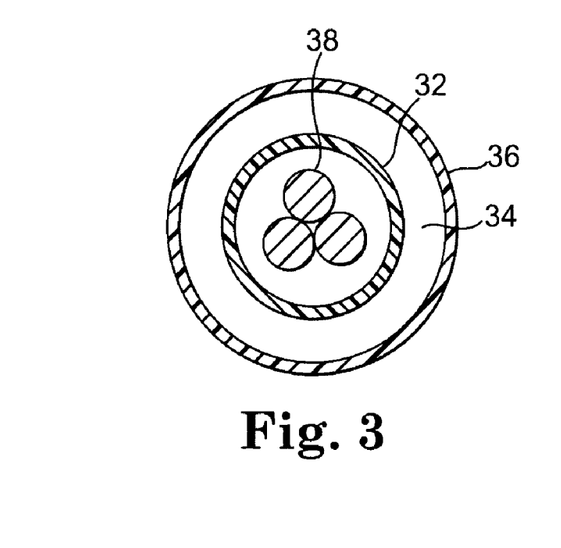
FIG. 3 is a cross-sectional end view taken along section line 3-3 of FIG. 2, with the cylinder in its unpressurized condition.
Figure 4:
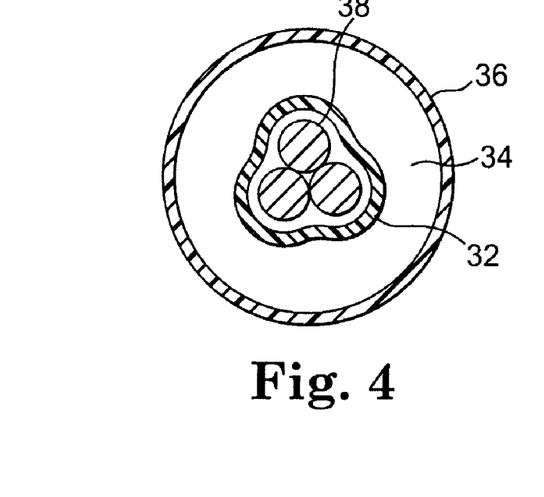
FIG. 4 is a cross-sectional end view taken along section line 3-3 of FIG. 2, with the cylinder in an exemplary pressurized condition.

FIG. 2 illustrates an implantable and inflatable penile prosthesis device 30 similar to that of FIG. 1, but with an alternative structure within an interior cavity 34 of a body portion 36. In particular, the interior cavity 34 includes a closed cylinder 32 that is sealed or closed from the surrounding environment of the cavity 34 and contains at least one elongated filament or structure 38 that extends along at least a portion of the length of the cylinder 32, and more preferably contains at least two elongated filaments 38 that are twisted or otherwise positioned relative to each other to create a desired strength within the cylinder 32. As illustrated, the length of each of the filaments 38 is substantially greater than the diameter of these filaments. Further, while the filaments may have a circular cross-section (such as is shown in FIGS. 3 and 4), the filaments 38 may instead have a different cross-sectional shape, such as oval, square, rectangular, triangular, or any other desired shape in which the filaments can be produced.

The number and type of filaments used should be chosen or designed to provide a structure that gives a desired rigidity to the body portion 36, both when it is inflated and when it is deflated. In this particular illustrated embodiment, the cylinder 32 is provided with three filaments 38 that extend generally from a proximal end 40 to a distal end 42 of the cylinder 32 and are twisted relative to each other along the length of the cylinder 32. Alternatively, the filaments may be arranged relative to each other in another configuration, such as braided, coiled, or otherwise arranged. The filaments 38 may be secured to one or both ends 40, 42 of the cylinder 32, if desired, to keep the filaments in predetermined or desirable positions relative to each other and relative to the cylinder 32.

The filaments 38 may be selected from a variety of materials that are relatively flexible yet provide a desired level of rigidity within the body portion 36. Materials from which the filaments may be made include cloth or plastic rope or rope-like materials, wire, metal fibers, plastic filaments, springs, coils, and the like. Alternatively, a plurality of individual members or portions can be attached in a string-like manner to make up a filament 38. With any of these alternatives, the filaments 38 can extend along the entire length of the cylinder 32 and body portion 36, or may extend only along a portion of the length of these components. Each filament may comprise a single material, or may include a number of strands or portions woven or secured together to make up a single filament. Similarly, the diameter of the filaments 38 may vary widely, and depends at least partially on the material from which the filaments are made and the desired amount of flexibility of the filaments 38 within the structure.

In accordance with the exemplary embodiment illustrated in FIG. 2, the cylinder 32 is preferably made of a material that is relatively compressible so that it can collapse and conform to the filaments 38 when fluid is transferred to the interior cavity 34 through a tube 42. Additionally referring now to FIGS. 3 and 4, the cylinder 32 is shown in its unpressurized or uncompressed state in FIG. 3, where there is little or no fluid within the interior cavity 34, then in its pressurized or compressed form in FIG. 4, where the fluid transferred under pressure to the interior cavity 34 through the tube 42 causes the walls of the cylinder 32 to compress and conform to the outer structure of the filaments 38. When the cylinder 32 is compressed, it generally molds to the outer structure of the twisted filaments 38, thereby binding the filaments and cylinder into a rigid structure and effectively preventing or limiting relative movement between the filaments. This filament-containing cylinder configuration thereby provides more rigidity to the body portion 36 than a similar fluid-filled structure that depends only on fluid volume and pressure to maintain structural rigidity. The cylinder 32 may then expand back to its uncompressed state, as shown in FIG. 3, after the pressurized fluid exits the interior cavity 34. Depending on the filaments chosen and the filament arrangement used, the filaments may be relatively free or movable relative to each other when the cylinder 32 is not compressed, which can provide additional flaccidity to the cylinder 32 and the corresponding body portion 36. In accordance with the advantages of the present invention, the filament-containing cylinder structure of this embodiment fills a portion of the internal volumetric capacity of the cavity 34 to provide a device that is at least slightly more rigid, even in its deflated state, than a cavity containing no such structure. This device also advantageously requires a lower volume of fluid transfer for inflation and deflation since the filament-containing cylinder 32 occupies a portion of the volume of the interior cavity 34.

The cylinder 32 may be fixed or secured to the interior cavity 34 at either the proximal end 40 of cylinder 32, the distal end 42 of cylinder 32, or both the proximal and distal ends 40, 42 of cylinder 32. Such securing of the cylinder 32 within the cavity 34 is optional, however, particularly in cases where the length of the cylinder 32 is similar to the length of the cavity 34 so that movement of the cylinder 32 relative to the cavity would be relatively unlikely. In cases where the volume of the cylinder 32 is relatively small as compared to the interior volume of the cavity 34, it may be particularly desirable to secure the cylinder 32 within the cavity 34 in order to prevent the cylinder 32 from bending or otherwise deforming within the cavity 34. Similarly, the bladder 20 of FIG. 1 may be secured at either or both ends within the interior cavity 14 of the body portion 12.

Figure 5:
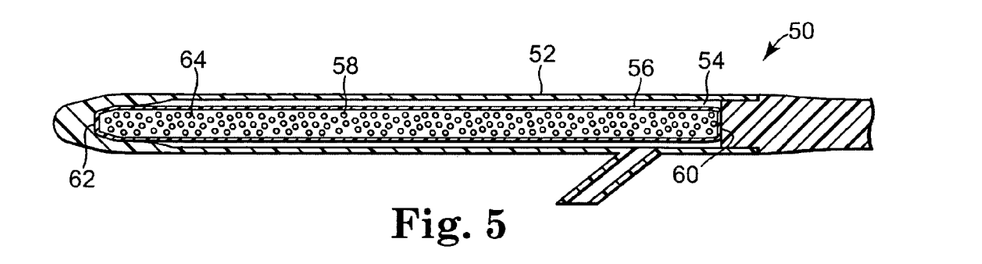
FIG. 5 is a cross-sectional side view of another embodiment of an implantable penile prosthesis device, including a particle chamber in its expanded condition.
Figure 6:
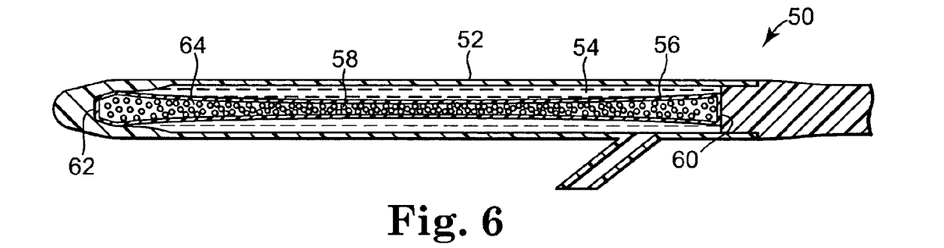
FIG. 6 is a cross-sectional side view of the device of FIG. 5, with the particle chamber in its compressed condition.

FIGS. 5 and 6 illustrate another embodiment of an implantable and inflatable penile prosthesis device 50 including a body portion 52 having an interior cavity 54. In particular, the interior cavity 54 includes a particle chamber 56 that is sealed or closed from the surrounding environment of the cavity 54. The particle chamber 56 contains a plurality of particles or elements 58 dispersed throughout at least a portion of the length of the particle chamber 56, and more preferably contains at least enough particles 58 to create a desired flexibility and strength within the particle chamber 56. As illustrated, the particles 58 are distributed with a relatively uniform density throughout the internal portion of the particle chamber 56; however, the particle density may instead vary in different areas of the particle chamber 56. When it is desired to maintain such a varying particle density, the chamber 56 may be subdivided into multiple chambers that each have particular particle densities, such as when it is desirable for certain portions of the device 50 to have different characteristics than other portions of the device 50 (e.g., differing rigidities along its length). In this particular illustrated embodiment, the particle chamber 56 is provided with a plurality of particles 58 dispersed randomly from a proximal end 60 to a distal end 62 of the chamber 56.

The particles 58 may be relatively spherical in shape with a circular cross-section as is shown in FIGS. 5 and 6. Alternatively, the particles 58 may have a different cross-sectional shape, such as oval, square, rectangular, triangular, or any other desired regular or irregular shape in which the particles 58 can be produced. Each of the particles 58 may be essentially identical in size, shape, and material as the other particles within a particular particle chamber 56, or a variety of differently sized and/or shaped particles 58 of the same or different materials may be dispersed within a single particle chamber 56. Alternatively, a plurality of individual particles 58 can be attached to one another in a cluster or grouping to make up a larger particle grouping within the chamber 56, where each of the particles within a cluster or grouping may be the same or different size, shape and material as the other particles within that cluster or grouping.

Materials from which the particles may be made include plastic, rubber, metal, and the like, where the materials may be relatively rigid or elastic, as desired and are preferably biocompatible materials. In some cases it may be advantageous for the particles to be relatively elastic so that they can compress and expand within the chamber 56 when exposed to differing amounts of external pressure. However, in other cases it may be desirable that the particles 58 do not change in dimensions in response to the application or removal of external pressures. With any of these alternatives, the particles 58 can be solid structures, or may comprise a wall structure surrounding an internal void or opening within the particle (e.g., a hollow sphere). If the particles 58 have such an internal void or opening, the opening may be filled with a compressible or incompressible fluid or other material or may be essentially empty. The structure of each particle and the materials from which the particles are made are preferably selected for inclusion within the chamber 56 depending on the particular performance characteristics that are desired from the device 50, as explained further below.

Preferably, the particles 58 are dispersed within some type of fluid or gel-like substance 64 so that they are suspended relatively uniformly throughout the chamber 56. That is, it is preferable that the particles do not "settle" or fall into one concentrated area of the chamber 56, such as may be caused by gravitational forces. Exemplary materials in which the particles may be dispersed include water, saline, gelatin or other gel materials, glycerin, oil, or the like, or any combination of such exemplary materials. The substance 64 may be compressible or incompressible when subjected to external pressure.

In accordance with the embodiment illustrated in FIGS. 5 and 6, the particle chamber 56 is preferably made of a material that is relatively compressible so that it can collapse and conform to the particles 58 when sufficient fluid is transferred to the interior cavity 54. The particle chamber 56 is shown in its unpressurized or uncompressed state in FIG. 5, where there is little or no pressurized fluid within the interior cavity 54. In this state of the device 50, the particles 58 are preferably relatively free to move relative to one another within the chamber 56 (and within any substance 64 in which it may be suspended), and the materials contained within the chamber 56 preferably allow the device 50 to be in its flaccid or deflated condition. FIG. 6 illustrates the device 50 in its rigid or erect condition. In this state of the device 50, the particle chamber 56 is pressurized or compressed by fluid that has been transferred into the interior cavity 54 under pressure, causing the walls of the chamber 56 to compress and at least partially conform to the particles 58. The amount of fluid provided to the cavity 54 is preferably controllable in such a way to initially fill the interior cavity 54 without any compression of the chamber 56, then to provide the necessary volume of fluid to the cavity 54 to compress the chamber 56 by a desired amount. That is, when the chamber 56 is compressed by fluid pressure within the interior cavity 54, it generally molds to the outer structure of the particles 58, thereby binding the particles 58 and chamber 56 into a rigid structure and effectively preventing or limiting relative movement between the particles 58. Thus, the volume of transferred fluid can provide varying levels of rigidity to the device 50.

When it is desired to return the device 50 to its flaccid or deflated state, a pump or other device may be used to force the pressurized fluid from the interior cavity 54. The chamber 56 may then expand back to its uncompressed state, as shown in FIG. 5. It is therefore preferable that the particle chamber 56 is made of a material that is relatively elastic so that it can return to its original (or "equilibrium") condition when the external pressure is removed or reduced. Depending on the particles chosen and the particle arrangement used, the particles may be relatively free or movable relative to each other when the chamber 56 is not compressed, which can provide additional flaccidity to the chamber 56 and the corresponding body portion 52. In accordance with the advantages of the present invention, the particle-containing chamber 56 of this embodiment fills a portion of the internal volumetric capacity of the cavity 54 to provide a device that is at least slightly more rigid, even in its deflated state, than a cavity containing no such structure. This device also advantageously requires a lower volume of fluid transfer for inflation and deflation since the particle-containing chamber 56 occupies a portion of the volume of the cavity 54. Thus, the number and type of particles 58 contained within particle chamber 56 along with any other materials contained therein, such as substance 64, should be chosen or designed to provide a structure that gives a desired rigidity to the body portion 52 when in its inflated and deflated conditions.

The particle chamber 56 may be fixed or secured to the interior cavity 54 at either the proximal end 60 of particle chamber 56, the distal end 62 of chamber 56, or both the proximal and distal ends 60, 62 of chamber 56. Such securing of the chamber 56 within the interior cavity 54 is optional, although attaching the chamber near at least one end may prevent movement of the particle chamber 56 relative to the cavity 54, such as to prevent the particle chamber 56 from bending or otherwise deforming within the interior cavity 54. Further, the manner in which the particle chamber 56 is secured within the cavity 54 may provide different characteristics or properties to the device 50, particularly when the chamber is compressed, as in FIG. 6. As shown in this Figure, the ends of the chamber 56 are secured within the cavity in such a way that the center area of the chamber compresses and changes dimensions, while the ends of the chamber remain fixed in their original position. Alternatively, a smaller portion of the chamber may be attached, such as just a point at the tip of the chamber, thereby allowing for more even compression along the entire length of the chamber 56.

Figure 7:
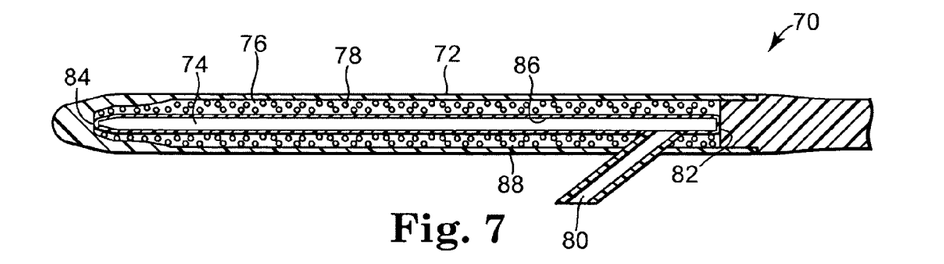
FIG. 7 is a cross-sectional side view of another embodiment of an implantable penile prosthesis device, including a particle chamber that surrounds a fluid-receiving cavity, where the particle chamber is shown in its expanded condition.
Figure 8:
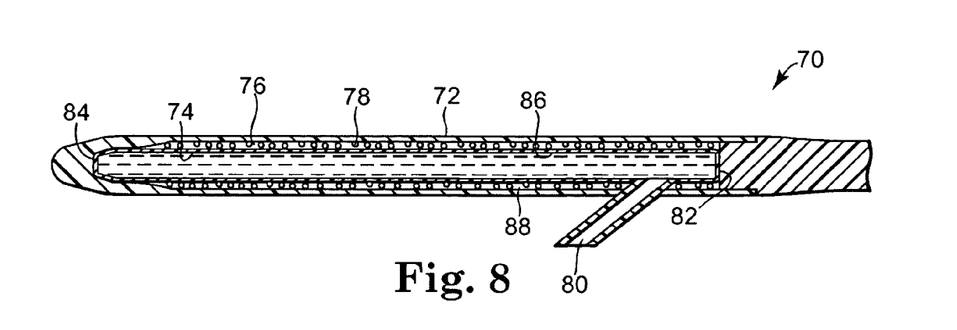
FIG. 8 is a cross-sectional side view of the device of FIG. 7, with the particle chamber shown in its compressed condition.

FIGS. 7 and 8 illustrate another exemplary embodiment of an implantable and inflatable penile prosthesis device 70, including a body portion 72 having an interior cavity or tube 74 that is at least partially surrounded by a particle chamber 76. The particle chamber 76 is preferably sealed or closed from the interior cavity 74 and contains a plurality of particles or elements 78 dispersed throughout at least a portion of the length of the particle chamber 76. More preferably, particle chamber 76 should contain enough particles 78 to create a desired strength and flexibility within the prosthesis device 70, both in its inflated or deflated condition.

The particle chamber 76 of this embodiment is preferably a continuous, hollow cylindrical compartment that extends along at least a portion of the length of the body portion 72. Preferably, the chamber 76 extends within most of the length of the body portion 72 and surrounds approximately the entire length of the interior cavity 74, although the interior cavity or tube 74 may be either longer or shorter than the particle chamber 76. While it is further preferable that only a single, elongated particle chamber is provided within the body portion 72, it is possible that multiple particle chambers are provided or that the particle chamber 76 is divided into multiple sections along the length of the device 70, where each section or chamber may contain the same or different materials as the other sections or chambers. In some cases, it may be desirable for certain areas of the body portion 72 to have different characteristics (e.g., rigidity) than other areas of the body portion 72. Thus, if multiple sections or chambers or provided, they may be filled with different amounts and types of materials to achieve those desired characteristics.

The interior cavity 74 is fluidly connected to some type of pump assembly and/or reservoir through a tube 80 for transfer of fluid to and from the device 70. The tube 80 extends from the body portion 72 and is preferably sized for efficient transfer of fluid. As shown in FIGS. 7 and 8, the tube 80 extends through the side or wall of the particle chamber 76. However, the tube 80 may be located at any position along the body portion 72 and may, for example, be positioned at either the proximal end 82 or distal end 84 of the interior cavity 74 for direct communication with the interior cavity 74, without extending through the particle chamber 76.

The particle chamber 76 is shown in its unpressurized or uncompressed state in FIG. 7, where there is little or no fluid within the interior cavity 74. In any of the embodiments of the present invention, however, a fluid-receiving cavity or chamber may be at least partially filled with a fluid to maintain a desired fullness of the penile prosthesis device, even when complete rigidity is not desired. In the state of the device 70 shown in FIG. 7, the particle chamber 76 is in its unpressurized state, where the particles 78 are preferably relatively free to move relative to one another within the chamber 76, and the materials contained within the chamber 76 preferably allow the device 70 to be in a flaccid or deflated condition.

FIG. 8 illustrates the device 70 with the particle chamber 76 in its pressurized or compressed condition, where fluid has been transferred into the interior cavity 74 under pressure. The pressure of the fluid in the cavity 74 presses against the walls of the particle chamber 76, preferably providing additional rigidity to the body portion 72 through the compression of the particle chamber 76 around the particles 78. The fluid transfer is preferably controllable so that the chamber 76 is compressed by an amount that allows the chamber 76 to at least partially conform to the materials contained within the chamber 76, such as the particles 78.

The volume capacity of the particle chamber 76 and the interior cavity 74 are preferably selected to provide the user with the desired rigidity and fullness of the body portion 72 in each state or condition of the particle chamber 76 (e.g., compressed and uncompressed states) while minimizing the amount of fluid that must be transferred to and from the interior cavity 74. Further, the particle chamber 76 may be a discrete component that is positioned within the body portion 72, or the particle chamber may instead be formed by utilizing the outer wall of the body portion 72 as its outer wall. In any case, it is preferable that the particles 78 are dispersed within some type of fluid or gel-like substance 88 so that they are suspended and distributed throughout the particle chamber 76. The substance 88 may be compressible or incompressible when subjected to external pressure.

Figure 9:
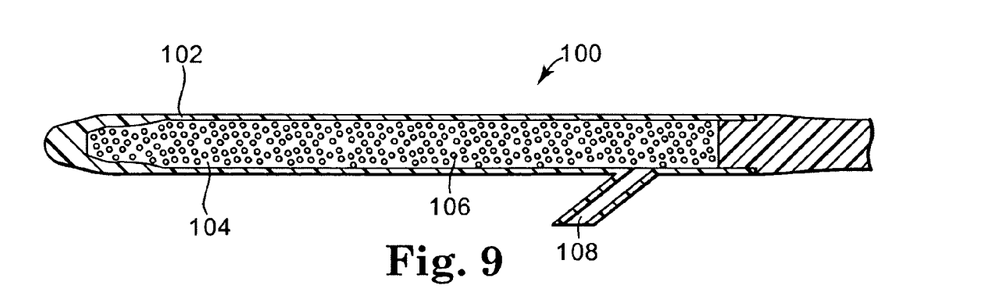
FIG. 9 is a cross-sectional side view of another embodiment of an implantable penile prosthesis device of the present invention, including a plurality of volume-displacing particles dispersed through the length of the device.

FIG. 9 illustrates another embodiment of an implantable and inflatable penile prosthesis device 100 that includes a body portion 102 having an interior cavity 104 that is in fluid communication with a reservoir through a fluid tube 108. The interior cavity 104 contains at least one particle or substance 106 that displaces a portion of the interior volume of the cavity 104 to minimize the amount of fluid transfer necessary for changing the condition of the body portion 102 (e.g., to increase the rigidity of the body portion 102 when filled with fluid). The particles 106 may be of any size, shape, and material that provides the desired volume displacement, and may be suspended within a suspension material, if desired. For example, the particles may be beads, balls, wires, coils, 3-dimensional regular or irregular shaped objects, and the like. In any case, it is preferable that the materials within the cavity 104 do not migrate from the cavity 104 into the fluid tube 108, but are instead permanently retained within the cavity 104. This may be accomplished by providing particles 106 that are larger than the interior dimensions of the fluid tube 108, by providing a screen or other device that partially blocks the movement of particles or substances 106 into and out of the tube 108, or by some other method or device.

Figure 10:
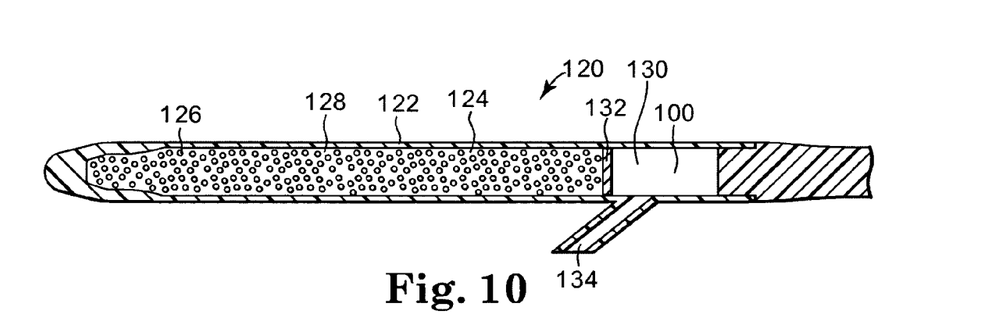
FIG. 10 is a cross-sectional side view of another embodiment of an implantable penile prosthesis device having an internal chamber divided into two sections by a moveable member, with a particle-containing chamber portion shown in its expanded condition.
Figure 11:
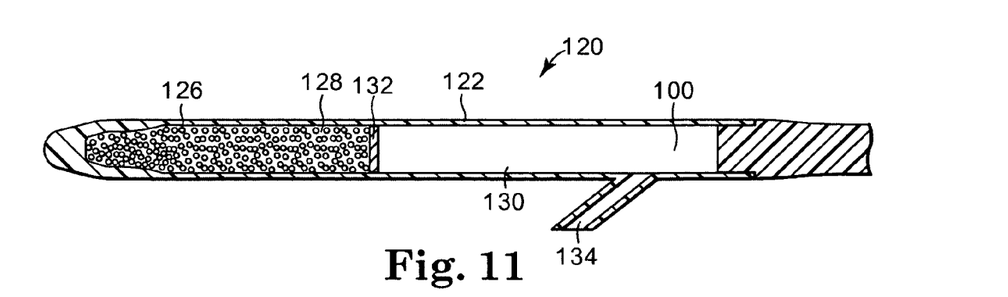
FIG. 11 is a cross-sectional side view of the device of FIG. 10, with the particle-containing chamber portion shown in its compressed condition.

Another exemplary penile prosthesis device 120 is illustrated in FIGS. 10 and 11, which generally includes a body portion 122 having an interior cavity 124 that contains a plurality of particles 126. This embodiment is similar to that of FIG. 9 in that the particles 126 are contained within the interior cavity 124 itself, rather than within a separate chamber that is positioned within the interior cavity 124. However, it is contemplated that device 120 may include a chamber (not shown) in which the particles are contained. In addition, the particles or materials 126 may be dispersed within some type of fluid or gel-like substance. The interior cavity 124 of the device 120 is divided into a first chamber 128 and a second chamber 130, with a moveable plunging device 132 separating the two chambers. The first chamber 128 may be filled or partially filled with materials 126 that are preferably at least somewhat compressible. This first chamber 128 is not in direct fluid communication with the fluid entering the body portion 122 through a fluid tube 134. The second chamber 130 may also contain materials or particles (not shown), which preferably cannot migrate out of the chamber 130 and into the fluid tube 134.

The moveable plunging device 132 is preferably designed to completely separate the first and second chambers 128, 130 so that materials, such as fluids and/or particles, cannot move between the chambers 128, 130. The device 132 may be a cylinder, a ball, or the like, that provides a fluid-tight seal between the outer surface of the device 132 and the inner wall of the interior cavity 124. In this embodiment, a fluid or gaseous media enters the second chamber 130 through the fluid tube 134 under sufficient pressure to move the device 132 toward the first chamber 128. This movement of the device 132 decreases the internal volume of the chamber 128 and increases the density of the materials within the first chamber 128. If the materials or particles 126 within the first chamber 128 are compressible, the pressure caused by movement of the device 132 may also compress the materials. This compression and/or increased density of the particles or materials 126 will provide more rigidity to the body portion 122 than if no such particles were contained in the first chamber 128. The second chamber 130 may also contain materials other than the transferred fluid, if desired.

The first chamber 128 may optionally include a compression spring that extends along at least a portion of the chamber 128. Preferably, such a spring should extend along a sufficient length of the first chamber 128 so that it can urge the plunging device 132 back toward the second chamber 130 when the pressure is reduced on the device 132. This may happen, for example, after sufficient fluid is transferred out of the second chamber 130 to reduce the pressure on the device 132. Thus, it is advantageous to select a spring member that is weak enough to allow movement of the device 132 toward the first chamber 128 with the addition of fluid to the second chamber 130 and that is strong enough to urge the device 132 toward the second chamber 130 when fluid exits the second chamber 130. Without such a compression spring, the device 132 may be moved back toward the second chamber 130 due to the expansion of the materials 126 within the chamber 130, by the use of additional springs or devices in the second chamber 130, or through the use of some other mechanism.

Figure 12:
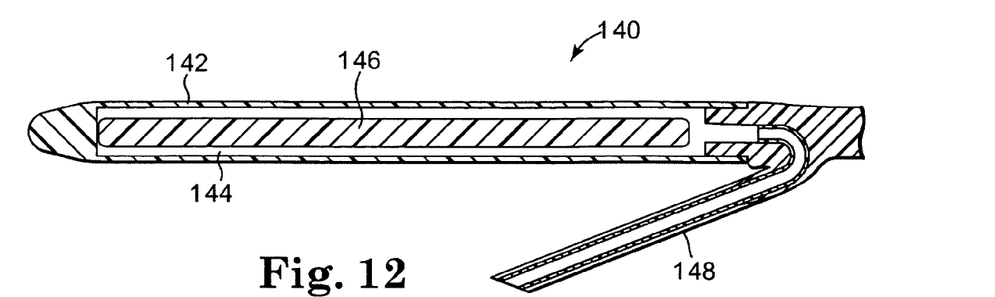
FIG. 12 is a cross-sectional side view of another embodiment of an implantable penile prosthesis device having an internal volume-displacing core member.

FIG. 12 illustrates another exemplary embodiment of an implantable and inflatable penile prosthesis device 140 of the present invention, the device 140 including an outer cylinder 142 having an interior cavity 144 and a member 146 that partially fills the internal volume of the cavity 144. Fluid is transferred to and from the cavity 144 through a tube 148 to fill and empty the outer cylinder 142, as desired. As with the other embodiments of the invention, the use of a member 146 within the cavity 144 decreases the volume of fluid that must be transferred to and from the cavity 144 to change the condition of the device 140. That is, the member 146 occupies the space that would otherwise need to be filled with fluid during an inflating process. The member 146 may be shaped as a cylinder with a constant diameter along its length, or may instead have a varying diameter along its length. Alternatively, the member 146 may have a different cross-section, such as square, triangular, oval, rectangular, or any other cross-sectional shape that is sized to fit within the cavity 144 and provide the desired characteristics for the device 140.

Regardless of the shape of the member 146, it may have the same or varying dimensions and/or shapes along its length. Further, the member 146 may have zones of varying stiffness along its length, as desired. The member 146 may be a solid, homogeneous member, or may instead have a core that is hollow or made of a material that differs from the outer material of the member. If the member 146 is hollow, the hollow portion may function as a reservoir for optionally containing a fluid or other substance. The member 146 may be at least slightly compressible when subjected to pressure, such as the pressure provided by the introduction of fluid to the inner cavity 144 through the tube 148. Further, the member 146 may be malleable or shapeable to allow the user to manipulate the device 140, as desired.

Figure 13:
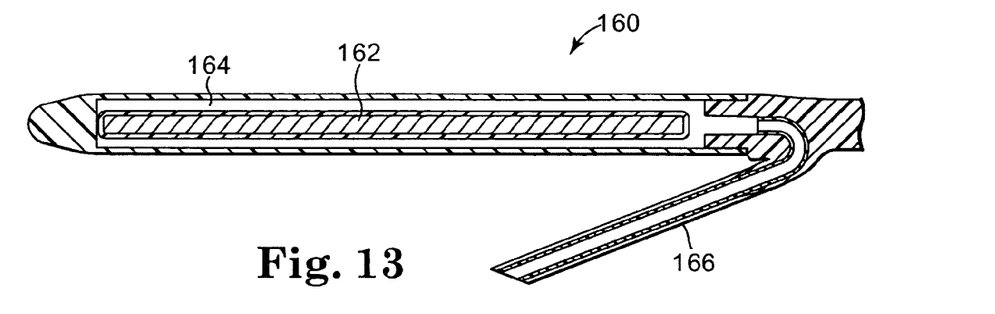
FIG. 13 is a cross-sectional side view of another embodiment of an implantable penile prosthesis device having an internal volume-displacing coiled tube member.

FIG. 13 illustrates a penile prosthesis device 160 that is similar to that of FIG. 12; however, in this embodiment, the device 160 includes a coiled tube 162 extending along the length of its interior cavity 164. The coiled tube 162 may include a wire or other elongated material wrapped around an internal core, such as, for example, the member 146 of FIG. 12. Alternatively, the coiled tube 162 may be a discrete component with enough structural integrity for it to maintain its shape without an internal core. The tube 162 may be a fluid reservoir for containing a fluid or other substance that may or may not be compressible, if desired. In any case, the material from which the coiled tube 162 is made may have any desired cross-sectional size and shape that provides particular characteristics to the device 160. In this embodiment, the pressure on the coiled tube 162 will be increased when fluid is added to the interior cavity 164 through a fluid tube 166, which preferably causes contraction of the coiled tube 162. Similarly, removal of fluid from the interior cavity 164 preferably causes the pressure on the coiled tube 162 to decrease, which will thereby cause elongation or expansion of the coiled tube 162.

Figure 14:
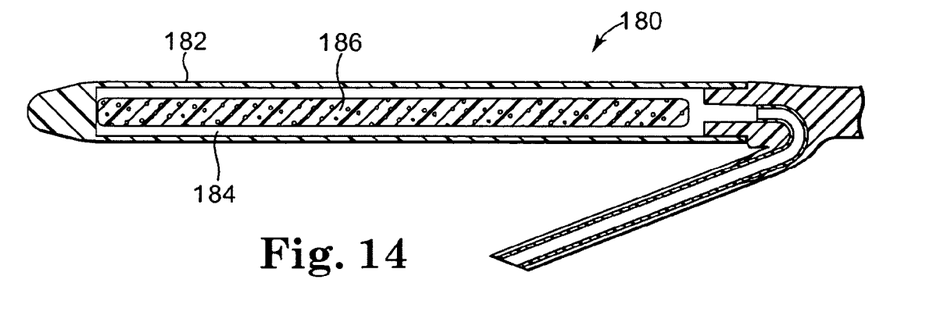
FIG. 14 is a cross-sectional side view of another embodiment of an implantable penile prosthesis device having an internal volume-displacing compressible core member.

Another exemplary embodiment of a penile prosthesis device 180 is illustrated in FIG. 14, which includes a body portion 182 having an interior cavity 184. Again, this device is similar to that of FIG. 12; however, in this embodiment, the device 180 includes a compressible core member 186 within its interior cavity 184. The core member 186 may be a large cell foam or fibrous material with a significant volume of voids throughout its structure. In this way, the core member 186 will preferably be relatively compressible when subjected to external pressure, such as the pressure provided by the fluid or other material that is transferred to the cavity 184. This compression of the member 186 will provide additional stiffness to the device 180 beyond the level of stiffness that is provided from the additional fluid volume in the cavity 184. As with many of the other embodiments of the present invention in which a volume-displacing material or member is used, the member 186 advantageously performs as a volume-displacing member that helps to provide a feeling of fullness to the device 180, even when in its flaccid condition. It is preferable that the core member 186 will expand toward is uncompressed size and shape when the external pressures are reduced or removed, and is even more preferable that the expansion of the core member 186 will force fluid from the interior cavity, thereby allowing for quicker deflation of the body portion 182. The core member 186 may be a foam, gel, or the like, which may be made of a wide variety of materials, such as silicone, cellulose, and the like. The selection of the material or materials of the core member 186 depends upon the desired characteristics of the device 180 in which it will be positioned.

Figure 15:
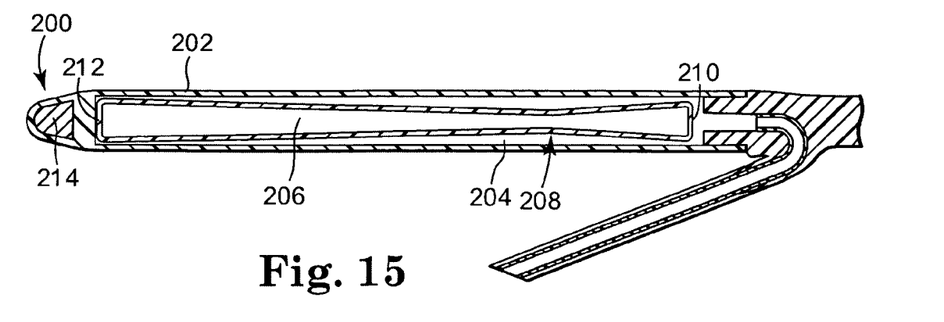
FIG. 15 is a cross-sectional side view of another embodiment of an implantable penile prosthesis device, including a hinged area to provide additional flexibility to the device.

FIG. 15 illustrates another embodiment of an implantable penile prosthesis device 200 including a body portion 202 having an interior cavity 204. Device 200 further includes an elongated volume-displacing member 206 within the cavity 204, with the member 206 having a hinge area 208 that can provide additional flexibility to the body portion 202 in that area. In this embodiment, the member 206 tapers down in size from a proximal end 210 of the interior cavity 204 toward the hinge area 208, and similarly tapers down in size from a distal end 212 of the interior cavity 204 toward the hinge area 208.

The hinge area 208 is a defined area of weakness about which the body portion 202 can more easily bend, which thereby provides increased flexibility for the device 200. Preferably, the hinge area 208 will be located in the patient in approximately the base area of the pendulous, which can provide the advantage of improving the flaccidity of the device when it is in its uninflated condition. This can also advantageously provide a more natural feel for the user. However, the hinge area 208 should not detrimentally change the structural rigidity of the device 200 when it is in its inflated or erect condition.

The member 206 may be made of a wide variety of compressible or incompressible materials and may be configured in a wide variety of ways, such as a solid cylinder, hollow tube, or the like. The member 206 may be tapered as shown in FIG. 15, but may instead have a constant cross-sectional shape and size along its length. The member 206 may also include any of the various shapes and materials of volume-displacing members described with regard to the other embodiments of the present invention, with the addition of a hinged area for this embodiment. It is also contemplated that the differentiated sections of the member 206 on either side of the hinge 208 may have different properties from each other, such as to give different rigidities to the device 200 along its length. The member 206 may also include more than one hinged area along its length, if desired.

The device 200 may further include an optional weighted tip portion 214 adjacent to the distal end 212 of the cavity 204. The amount of extra weight added at the tip portion 214 is preferably large enough to urge the body member 202 to bend downward at the hinge 208 when the device 200 is in its flaccid condition. However, the weight should not be so large that it is difficult for the body member 202 to become rigid when fluid is added to the cavity 204. A weighted tip portion or area may also be used as desired in accordance with any of the other embodiments of the present invention to urge the body member downward when in its flaccid condition.

Figure 16:
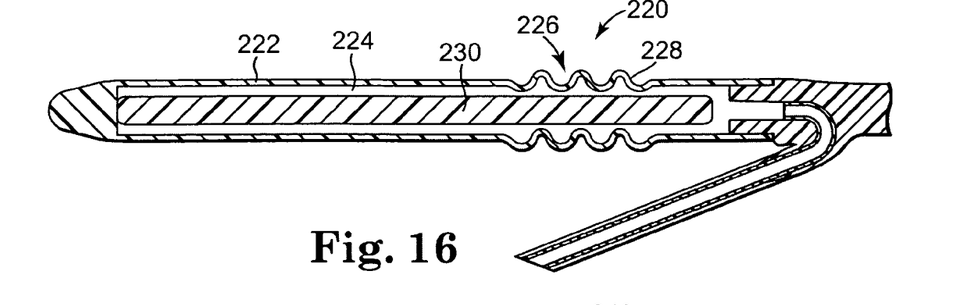
FIG. 16 is a cross-sectional side view of another embodiment of an implantable penile prosthesis device, including a varying flexibility zone or area in the outer body portion of the device.

FIG. 16 is another exemplary embodiment of an implantable penile prosthesis device 220 including a body portion 222 having an interior cavity 224. The body portion 222 includes a hinge area 226, which in this figure is shown as an accordion-type structure 228 on the outside wall of the body portion 222. The hinge area 226 may have a different configuration, however, to provide an area of the body portion that is relatively weak as compared to the rest of the body portion 222. The hinge area 226 will preferably be positioned in the patient proximate the base area of the pendulous, which can provide the advantage of improving the flaccidity of the device 220 when it is in its uninflated condition. Device 220 may optionally also include a compressible or incompressible elongated volume-displacing member 230 within the cavity 224 that may have a number of different configurations, such as those described herein relative to components positioned within a body portion of a penile prosthesis device. For one example, the member 230 may be a solid or hollow core cylinder that extends inside the cavity 224 along its length. Alternatively, the member 230 may also be provided with a hinged or weakened area of the type shown and described relative to FIG. 15. If the member 230 has such a hinged area, it would preferably be located in generally the same area as the hinge area 226 of the body portion 222 to further improve the flaccidity of the device in that area.

Figure 17:
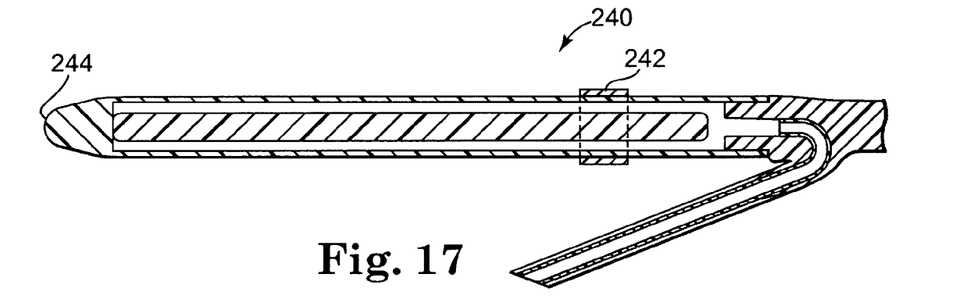
FIG. 17 is a cross-sectional side view of another embodiment of an implantable penile prosthesis device, including a stiffening segment for varying the flexibility of the device.
Figure 18:
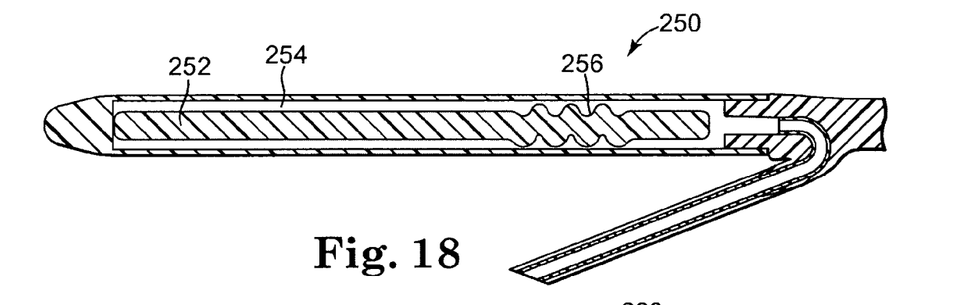
FIG. 18 is a cross-sectional side view of another embodiment of an implantable penile prosthesis device, with a varying flexibility zone or area in the core of the device.

FIG. 17 illustrates another embodiment of a penile prosthesis device 240 of the present invention, which shows an alternative configuration for improving the flexibility of the device 240 when in its flaccid condition. In particular, the device 240 is provided with a stiffening segment 242, which is preferably located proximate the base area of the user's pendulous to provide a particular or targeted area around which the device 240 may bend or flex. That is, the portion of the device 240 between a tip 244 and the stiffening segment 242 will tend to move downward when the device 240 is in its flaccid condition due to gravity, while the stiffening segment 242 will preferably be strong enough to prevent this area from moving downward. The stiffening segment 242 may be a separate strengthening material wrapped around the outside of the device 240, or may be integrated into the structure of the device 240. The device 240 may also include an optional volume-displacing member within its inner cavity to provide the device 240 with the characteristics described herein relative to other embodiments of the invention FIG. 18 illustrates yet another embodiment of a penile prosthesis device 250 of the present invention. The device 250 includes a volume-displacing member 252 located within an inner cavity 254. The member 252 includes a hinged or weakened area 256 similar to that of FIG. 15, however, the area 256 of this embodiment may be provided as a weakened area (e.g., an accordion-type structure) of the member 252 or as a stiffening segment of the member 252. In either case, the different structure of the member 252 in this area provides a targeted area about which the member 250 will tend to bend or flex. As with the other embodiments having a volume-displacing member with a defined bend or flex zone, the device 250 will preferably bend or flex more easily in this area 256 when the device is in its flaccid condition, but can remain relatively rigid when in its inflated or erect condition.

Figure 19:
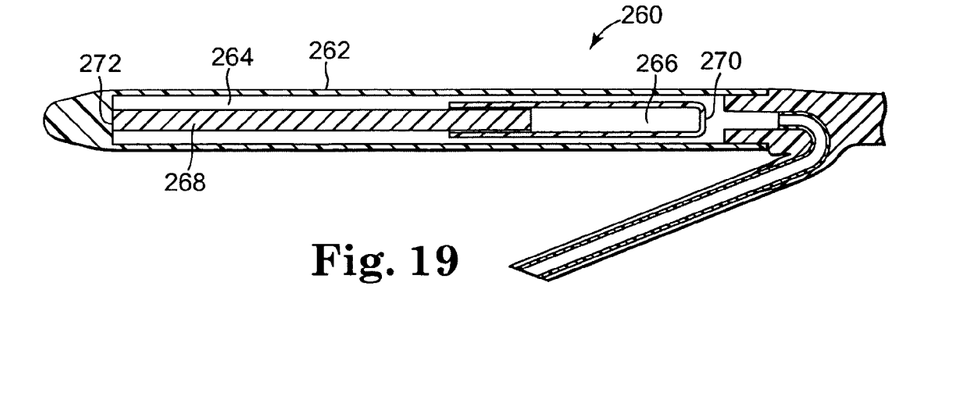
FIG. 19 is a cross-sectional side view of another embodiment of an implantable penile prosthesis device, including a telescoping feature.

FIG. 19 illustrates another embodiment of a penile prosthesis device 260 having a body portion 262 with an inner cavity 264. The device 260 further includes a hollow core member 266 that extends within a portion of the cavity 264, where the length of the member 266 is less than that of the cavity 264 when the device 260 is in its flaccid condition. As shown, the member 266 extends generally from a proximal end 270 of the cavity 264 toward a distal end 272 of the cavity 264. The device 260 further includes a mating core member 268 that can slide into the hollow area of core member 266, where the length of the member 268 is also less than the length of the cavity 264. As shown, the member 268 extends generally from a distal end 272 of the cavity 264 toward the proximal end 270 of the cavity 264. Preferably, the lengths of the members 266, 268 are selected so that member 268 is positioned at least partially within the member 266 in any condition of the device 260. The two members 266, 268 can slide relative to one another in a telescoping manner in response to the addition of fluid to the cavity 264. In another configuration of this embodiment, fluid may be added directly into the interior portion of the hollow member 266 to cause the sliding of the members 266, 268 relative to one another. The members 266, 268 thereby function as volume-displacing members, while also providing additional structural rigidity to the device 260. It is advantageous with this embodiment that the outer surface of the body portion 262 is expandable in length, such as may be accomplished by making the body portion from an expandable material, or as may be accomplished with an accordion-type structure for at least a section of the body portion 262.

An alternate embodiment of the present invention may include displacing volume within the corpora itself rather than within the cylinder. By using similar techniques to those described above to displace volume within the corpora, less blood is required to engorge the penis to obtain tumescence. A volume displacement device may be inserted into the corpora using a cannula or trocars as conduits to push or insert the volume displacement device at the desired locations. The volume displacement device may span the entire length or just portions of the corpora.

While the above embodiments each describe a single bladder, cylinder, or malleable member within an inflatable body portion, it is contemplated that any device of the present invention may include multiple bladders, cylinders, or malleable members arranged along the length of a single interior cavity. Further, a body portion may contain a combination of any of these types of devices that serve to partially fill the interior cavity of the body portions. If a particular device includes more than one bladder, cylinder, or other member, these elements may have the same or different characteristics from each other within a single cavity, as desired, to provide certain levels of rigidity to different parts of the device, for example.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

The invention claimed is:

1. A penile prosthesis device comprising:
   a generally cylindrical body portion comprising a cavity with an inner wall, a proximal end, a distal end, and at least one volume-displacing member occupying at least a portion of the cavity and comprising a bladder containing a volume of fluid, wherein the at least one volume-displacing member is smaller in at least one dimension than the dimensions of the cavity to provide an internal chamber at least partially surrounding the at least one volume-displacing member and adjacent to the inner wall of the cavity; and
   a fluid transfer tube extending from the body portion for transferring fluid to and from the internal chamber;
   wherein the device is convertible from a flaccid condition to a rigid condition when a sufficient volume of fluid is transferred into the internal chamber to substantially fill the internal chamber.

2. The penile prosthesis device of claim 1, wherein the device in its flaccid condition comprises the internal chamber having a first volume and the device in its rigid condition comprises the internal chamber having a second volume that is larger than the first volume, and wherein a volume of the cavity is the same when the device is in its flaccid condition and in its rigid condition.

3. The penile prosthesis device of claim 1, wherein the internal chamber is annular.

4. The penile prosthesis device of claim 1, wherein the bladder is at least partially compressible when a volume of fluid is transferred into the internal chamber.

5. The penile prosthesis device of claim 1, wherein the at least one volume-displacing member further comprises a plurality of particles.

6. A penile prosthesis device comprising:
   a generally cylindrical body portion comprising a cavity with an inner wall, a proximal end, a distal end, and at least one volume-displacing member occupying at least a portion of the cavity, wherein the at least one volume-displacing member is smaller in at least one dimension than the dimensions of the cavity to provide an internal chamber at least partially surrounding the at least one volume-displacing member and adjacent to the inner wall of the cavity and wherein the volume-displacing member comprises a closed cylinder containing at least two elongated members extending along at least a portion of the length of the closed cylinder and positioned relative to each other within the cylinder to provide a predetermined flexibility, rigidity and strength to the body portion; and
   a fluid transfer tube extending from the body portion for transferring fluid to and from the internal chamber;
   wherein the device is convertible from a flaccid condition to a rigid condition when a sufficient volume of fluid is transferred into the internal chamber to substantially fill the internal chamber.

7. The penile prosthesis device of claim 6, wherein the at least one volume-displacing member comprises a closed cylinder containing at least three elongated members extending along at least a portion of the length of the closed cylinder.

8. The penile prosthesis device of claim 6, wherein the closed cylinder comprises an outer wall that is collapsible to generally conform to the at least one elongated member contained within the closed cylinder when a sufficient amount of fluid is added to the internal chamber.

9. A penile prosthesis device comprising:
   a generally cylindrical body portion comprising a cavity with an inner wall, a proximal end, a distal end, and at least one volume-displacing member occupying at least a portion of the cavity and comprising a bladder containing a plurality of particles, wherein the at least one volume-displacing member is smaller in at least one dimension than the dimensions of the cavity to provide an internal chamber at least partially surrounding the at least one volume-displacing member and adjacent to the inner wall of the cavity; and
   a fluid transfer tube extending from the body portion for transferring fluid to and from the internal chamber;
   wherein the device is convertible from a flaccid condition to a rigid condition when a sufficient volume of fluid is transferred into the internal chamber to substantially fill the internal chamber.

10. The penile prosthesis device of claim 9, wherein the bladder further comprises a suspension material in which the plurality of particles is dispersed.

11. The penile prosthesis device of claim 9, wherein the bladder comprises an outer wall that is collapsible to generally conform to the plurality of particles within bladder when a sufficient amount of fluid is added to the internal chamber.

12. A penile prosthesis device comprising:
   a generally cylindrical body portion comprising a cavity with an inner wall, a proximal end, a distal end, and at least one volume-displacing member occupying at least a portion of the cavity, wherein the at least one volume-displacing member is smaller in at least one dimension than the dimensions of the cavity to provide an internal chamber at least partially surrounding the at least one volume-displacing member and adjacent to the inner wall of the cavity and wherein the cavity comprises a first cavity portion separated from a second cavity portion by a divider that is moveable between the proximal end and distal end of the cavity to change the ratio of a volumetric capacity of the first cavity portion relative to a volumetric capacity of the second cavity portion; and
   a fluid transfer tube extending from the body portion for transferring fluid to and from the internal chamber;
   wherein the device is convertible from a flaccid condition to a rigid condition when a sufficient volume of fluid is transferred into the internal chamber to substantially fill the internal chamber.

13. The penile prosthesis device of claim 12, wherein the first cavity portion comprises at least one material that is at least partially compressible.

14. The penile prosthesis device of claim 12, wherein the divider provides a fluid-tight seal between the first cavity portion and the second cavity portion.

15. The penile prosthesis device of claim 12, wherein the divider is moveable toward the first cavity portion in response to the addition of material to the second cavity portion.

16. A penile prosthesis device comprising:

a generally cylindrical body portion comprising a cavity with an inner wall, a proximal end, a distal end, and at least one volume-displacing member occupying at least a portion of the cavity, wherein the at least one volume-displacing member is smaller in at least one dimension than the dimensions of the cavity to provide an internal chamber at least partially surrounding the at least one volume-displacing member and adjacent to the inner wall of the cavity, and wherein the at least one volume-displacing member comprises an elongated member having a defined area of weakness with a lower strength than the rest of the elongated member to provide increased flexibility for the body portion adjacent the defined area of weakness; and a fluid transfer tube extending from the body portion for transferring fluid to and from the internal chamber;

wherein the device is convertible from a flaccid condition to a rigid condition when a sufficient volume of fluid is transferred into the internal chamber to substantially fill the internal chamber.

17. A penile prosthesis device comprising:

a generally cylindrical body portion comprising a cavity with an inner wall, a proximal end, a distal end, and at least one volume-displacing member occupying at least a portion of the cavity, wherein the at least one volume-displacing member is smaller in at least one dimension than the dimensions of the cavity to provide an internal chamber at least partially surrounding the at least one volume-displacing member and adjacent to the inner wall of the cavity, and wherein the at least one volume-displacing member comprises an elongated member having a stiffening segment that is less flexible than the rest of the elongated member to provide less flexibility for the body portion adjacent the stiffening segment; and a fluid transfer tube extending from the body portion for transferring fluid to and from the internal chamber wherein the device is convertible from a flaccid condition to a rigid condition when a sufficient volume of fluid is transferred into the internal chamber to substantially fill the internal chamber.

18. A penile prosthesis device comprising:

a generally cylindrical body portion comprising a cavity with an inner wall, a proximal end, a distal end, and at least one volume-displacing member occupying at least a portion of the cavity, wherein the at least one volume-displacing member is smaller in at least one dimension than the dimensions of the cavity to provide an internal chamber at least partially surrounding the at least one volume-displacing member and adjacent to the inner wall of the cavity, and wherein the volume-displacing member comprises a first hollow segment extending along at least a portion of the length of the cavity and a second segment extending along at least a portion of the length of the cavity, and wherein the second segment is at least partially inserted into the first segment and slideable relative to the first segment; and a fluid transfer tube extending from the body portion for transferring fluid to and from the internal chamber;

wherein the device is convertible from a flaccid condition to a rigid condition when a sufficient volume of fluid is transferred into the internal chamber to substantially fill the internal chamber.

19. A penile prosthesis device comprising:

a generally cylindrical body portion comprising a cavity with an inner wall, a proximal end, a distal end, and a particle chamber occupying at least a portion of the cavity, at least partially surrounding an internal chamber, and adjacent to the inner wall of the cavity, wherein the particle chamber contains a plurality of distinct particles dispersed throughout at least a portion of the length of the particle chamber; and a fluid transfer tube extending from the body portion for transferring fluid to and from the internal chamber;

wherein the device is convertible from a flaccid condition to a rigid condition when a sufficient volume of fluid is transferred into the internal chamber to substantially fill the internal chamber.

20. The penile prosthesis device of claim 19, wherein the particle chamber is a hollow cylindrical compartment that extends along at least a portion of the length of the cavity.

21. The penile prosthesis device of claim 19, wherein the device in its flaccid condition includes the internal chamber having a first volume and the device in its rigid condition includes the internal chamber having a second volume that is larger than the first volume.

* * * * *